(12) United States Patent
Zielinski

(10) Patent No.: US 8,414,626 B2
(45) Date of Patent: Apr. 9, 2013

(54) METHOD AND APPARATUS FOR LATERAL REDUCTION AND FUSION OF THE SPINE

(76) Inventor: Steven C. Zielinski, McGregor, TX (US)

( * ) Notice: Subject to any disclaimer, the term of this patent is extended or adjusted under 35 U.S.C. 154(b) by 31 days.

(21) Appl. No.: 13/074,997

(22) Filed: Mar. 29, 2011

(65) Prior Publication Data

US 2011/0178553 A1 Jul. 21, 2011

Related U.S. Application Data

(63) Continuation of application No. 11/363,607, filed on Feb. 27, 2006, now Pat. No. 7,914,562.

(51) Int. Cl.
*A61B 17/66* (2006.01)

(52) U.S. Cl.
USPC ...................................................... 606/282

(58) Field of Classification Search .......... 606/246–249, 606/257, 280–291, 70, 71, 902, 903, 99, 606/86 A, 279; 623/17.15–17.16
See application file for complete search history.

(56) References Cited

U.S. PATENT DOCUMENTS

| | | | |
|---|---|---|---|
| 4,611,581 A | 9/1986 | Steffee | |
| 5,180,381 A | 1/1993 | Aust et al. | |
| 5,324,290 A | 6/1994 | Zdeblick et al. | |
| 5,772,661 A | 6/1998 | Michelson | |
| 6,248,106 B1 | 6/2001 | Ferree | |
| 6,461,359 B1 * | 10/2002 | Tribus et al. | 606/247 |
| 6,764,489 B2 * | 7/2004 | Ferree | 606/279 |
| 6,830,570 B1 | 12/2004 | Frey et al. | |
| 6,923,814 B1 | 8/2005 | Hildebrand et al. | |
| 7,914,562 B2 | 3/2011 | Zielinski | |
| 2002/0091390 A1 | 7/2002 | Michelson | |
| 2003/0158553 A1 | 8/2003 | Michelson | |
| 2003/0187441 A1 | 10/2003 | Bolger et al. | |
| 2003/0208203 A1 * | 11/2003 | Lim et al. | 606/61 |
| 2004/0030346 A1 | 2/2004 | Frey et al. | |
| 2004/0092929 A1 | 5/2004 | Zindrick | |
| 2004/0225290 A1 | 11/2004 | Ferree | |
| 2006/0089644 A1 * | 4/2006 | Felix | 606/61 |
| 2006/0293670 A1 | 12/2006 | Smisson, III et al. | |
| 2007/0173842 A1 | 7/2007 | Abdou | |

FOREIGN PATENT DOCUMENTS

| | | |
|---|---|---|
| EP | 1488755 | 12/2004 |
| WO | 9627321 | 9/1996 |
| WO | 9841160 | 9/1998 |
| WO | 0101874 | 1/2001 |

OTHER PUBLICATIONS

Non-Final Office Action, U.S. Appl. No. 11/363,607, pp. 1-9.
Non-Final Office Action, U.S. Appl. No. 11/363,607, pp. 1-12.
Final Office Action, U.S. Appl. No. 11/363,607, pp. 1-13.
Advisory Action, U.S. Appl. No. 11/363,607, pp. 1-3.
Non-Final Office Action, U.S. Appl. No. 11/363,607, pp. 1-18.
Final Office Action, U.S. Appl. No. 11/363,607, pp. 1-12.

* cited by examiner

*Primary Examiner* — Sameh Boles
(74) *Attorney, Agent, or Firm* — Samuel M. Freund; Cochran Freund & Young LLC

(57) ABSTRACT

A method and device are provided for reducing abnormal vertebral orientation using a fixation plate that is used in conjunction with a positioning tool to reduce spinal deviation and properly position and secure adjacent vertebrae for fusion of the spine. The disclosed embodiments are particularly useful in minimally invasive surgical techniques such as laterally performed anterolisthesis and retrolisthesis.

17 Claims, 14 Drawing Sheets

_US 8,414,626 B2_

METHOD AND APPARATUS FOR LATERAL REDUCTION AND FUSION OF THE SPINE

RELATED CASES

This application is a Continuation Application of patent application Ser. No. 11/363,607, which was filed on Feb. 27, 2006, the disclosure and teaching of which application is hereby incorporated by reference herein.

BACKGROUND OF THE INVENTION

Fixation or fusion of individual vertebrae is frequently accomplished using rods and plates to secure bone grafts or implants between adjacent vertebral members. Conventional fusion techniques have failed in many instances to properly position the affected vertebrae for optimal fixation with respect to the graft.

SUMMARY OF THE INVENTION

An embodiment of the present invention may therefore comprise an apparatus for manipulating vertebral orientation and stabilizing spinal vertebrae comprising: a fixation plate having a central aperture and a plurality of first-end fastener holes and a plurality of second-end fastener holes positioned on opposing ends of the fixation plate; at least one fixed fastener that secures a first vertebrae through the first-end fastener holes to fixate position and rotation of the first-end of the fixation plate with respect to the first vertebrae; an adjustable fastener that secures a second vertebrae through the second-end fastener holes to temporarily fixate position and allow rotation of the second-end of the fixation plate with respect to the second vertebrae; a positioning tool that is keyed to interface with the aperture of the fixation plate and engages the aperture to adjust the orientation of the first vertebrae relative to the second vertebrae by transferring force from the positioning tool through the fixation plate to the first vertebrae and the second vertebrae; a stabilizer implanted between the first vertebrae and the second vertebrae through the aperture; the second-end fastener holes that facilitate repositioning of the adjustable fastener to vary the distance between the fixed fastener and the adjustable fastener to compress the stabilizer between the first vertebrae and the second vertebrae and rigidly secure position and rotation of the adjustable fastener to the second vertebrae.

An embodiment of the present invention may therefore comprise a method of manipulating vertebral orientation and stabilizing spinal vertebrae comprising: fixing position and rotation of a first-end of a fixation plate to a first vertebrae; temporarily fixing position and allowing rotation of a second-end of the fixation plate to a second vertebrae; engaging a central aperture on the fixation plate with a positioning tool that is keyed to interface with the central aperture; adjusting orientation of the first vertebrae with respect to the second vertebrae by transferring force from the positioning tool through the fixation plate to the first vertebrae and the second vertebrae; removing the positioning tool from the fixation plate; implanting a stabilizer between the first vertebrae and the second vertebrae through the aperture; releasing the temporary fixation of the adjustable fastener; compressing the stabilizer between the first vertebrae and the second vertebrae by adjusting a distance between the fixed fastener and the adjustable fastener; and, fixing the distance between first vertebrae and the second vertebrae by rigidly securing position and rotation of the adjustable fastener to the second vertebrae.

An embodiment of the present invention may also comprise device for manipulating vertebral orientation and stabilizing spinal vertebrae comprising: a fixation plate comprising plurality of first-end fastener holes and a plurality of second-end fastener holes positioned on opposing ends of the fixation plate; at least one fixed fastener that secures a first vertebrae through the first-end fastener holes to fix position and rotation of the first-end of the fixation plate with respect to the first vertebrae; an adjustable fastener that secures a second vertebrae through the second-end fastener holes to temporarily fix position and allow rotation of the second-end of the fixation plate with respect to the second vertebrae, the second-end fastener holes that facilitate repositioning of the adjustable fastener to vary the distance between the fixed fastener and the adjustable fastener and rigidly secure position and rotation of the adjustable fastener to the second vertebrae; and, a central aperture for transferring force from a positioning tool through the fixation plate to the first vertebrae and the second vertebrae, the central aperture that is of sufficient size to accommodate insertion of a stabilizer between the first vertebrae and the second vertebrae.

DETAILED DESCRIPTION OF THE INVENTION

Figure 1:
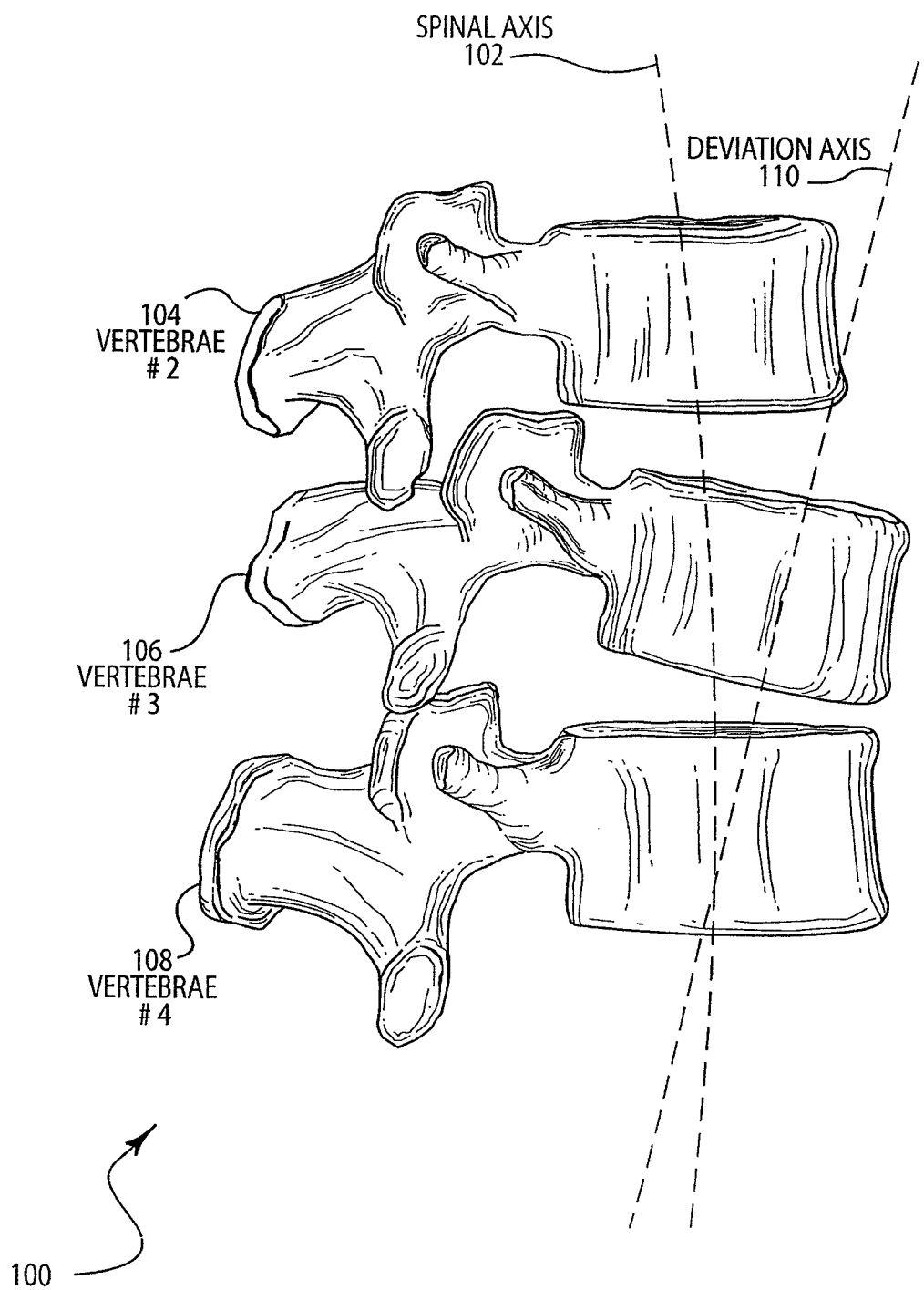
FIG. 1 is a lateral view of a section of spine experiencing abnormal vertebral orientation.

While this invention is susceptible to embodiment in many different forms, there is shown in the drawings and will be described herein in detail specific embodiments thereof with the understanding that the present disclosure is to be considered as an exemplification of the principles of the invention and is not to be limited to the specific embodiments described.

The disclosed embodiments provide a method and apparatus to reduce abnormal vertebral orientation using a fixation plate that is used in conjunction with a positioning tool to reduce the deviation and properly position and secure the adjacent vertebrae. These embodiments are useful in minimally invasive surgical techniques such as reduction of laterally performed anterolisthesis and retrolisthesis.

FIG. 1 depicts a lateral view of a section of lumbar spine experiencing abnormal vertebral orientation 100. As seen in FIG. 1 vertebrae #2 104, and vertebrae #4 108, are properly aligned on the spinal axis 102. Vertebrae #3 106 is experiencing abnormal vertebral orientation in a condition known as anterolisthesis. As can be seen in this example, vertebrae #3 106 is aligned on a deviation axis 110 which does not correspond to the spinal axis 102. In a circumstance such as this, intervertebral discs can be ruptured, herniated, torn, degenerated or otherwise rendered insufficient to support the vertebral column and spacing necessary between each vertebrae to permit nerve passage and articulation. Conditions like these can be caused by numerous factors such as trauma, disease, tumors, infections and other degenerative maladies and are often treated by stabilizing the vertebra adjacent to the affected intervertebral disc. This is often performed by fusing vertebra within the spine following vertebrectomy surgery or disectomy. When a disc (or portion thereof) is removed, a stabilizer such as a graft, mechanical implant or the like is introduced and placed in compression in the intervertebral space formerly occupied by the disc. Both the graft and vertebrae need to be positioned and stabilized so that a proper fusion of the involved section of the spine can take place. The procedure may also be used to implant an artificial disc where the fixation plate 112 is later removed to allow range of motion within the affected spine region.

Figure 2:
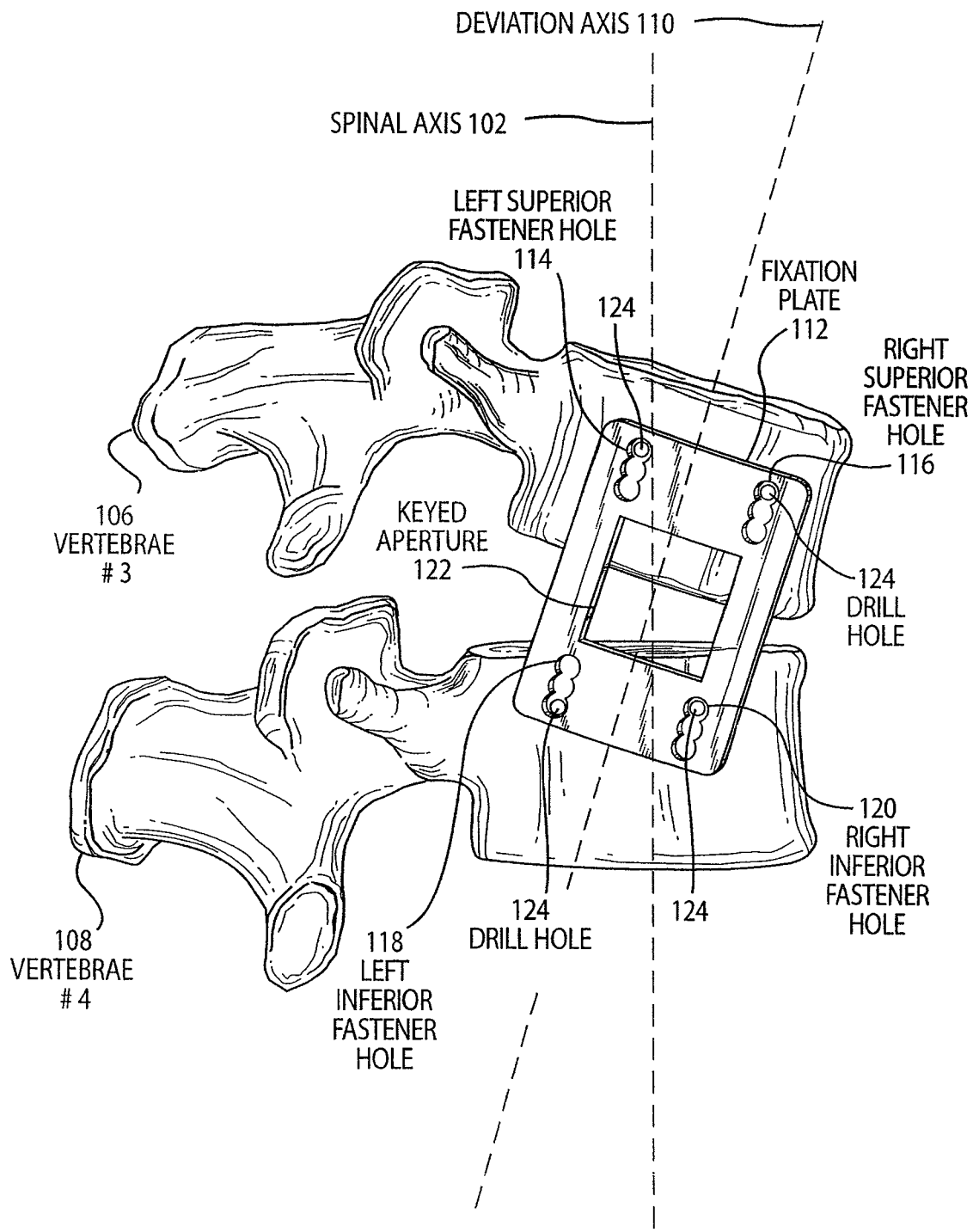
FIG. 2 is a lateral view of an embodiment of a fixation plate utilized for a lateral reduction and fusion of a section of a spine that is experiencing anterolisthesis.

FIG. 2 is a lateral view of an embodiment of a fixation plate utilized for a lateral reduction and fusion of a section the spine that is experiencing anterolisthesis. As can be seen in FIG. 2, a fixation plate 112 is positioned on the lateral aspect of the vertebral body of abnormally displaced vertebrae #3 106, anterior of the pedicle. Assuming in this case that the disc between vertebrae #3 106 and vertebrae #4 108 has already been removed by conventional means, proper alignment and spacing of these two adjacent discs is now performed. As illustrated, fixation plate 112 is positioned in general alignment with the deviation axis 110 of vertebrae #3 106. One or two drill holes 124 are bored into the vertebral body of vertebrae #3 106 corresponding to the position of left superior fastener hole 114 and/or right superior faster hole 116. Fasteners (detailed in later Figures) are then placed into the drill hole(s) and secured leaving a small gap between the head of the fastener and the fixation plate 112 to allow for rotational movement of the device. Once vertebrae #3 106 has been slideably attached to the fixation plate 112, the proper distance between the adjacent vertebrae can be set by positioning an additional drill hole 124 on vertebrae #4 108 corresponding with the right inferior fastener hole 120 of fixation plate 112. An additional fastener may then be placed into the drill hole 124 through the multi-positional right inferior fastener hole 120 and a secured similar to the fasteners secured into vertebrae #3 106 allowing rotational movement of the device. No fastener is placed in the left inferior fastener hole 118 at this time because the fixation plate 112 is not ultimately positioned with respect to vertebrae #4 108.

As stated above, the distance between the adjacent vertebrae is set by the relative position of the fixation plate 112 and the fasteners secured to the vertebrae. This distance and the aforementioned positioning is aided by incorporating a keyed aperture 122, through the fixation plate 112, allowing the surgeon visual and physical access to the intervertebral space. This opening may additionally facilitate the insertion or manipulation of the stabilizer (graft or implant) within the intervertebral space once the fixation plate 112 has been secured.

Figure 3:
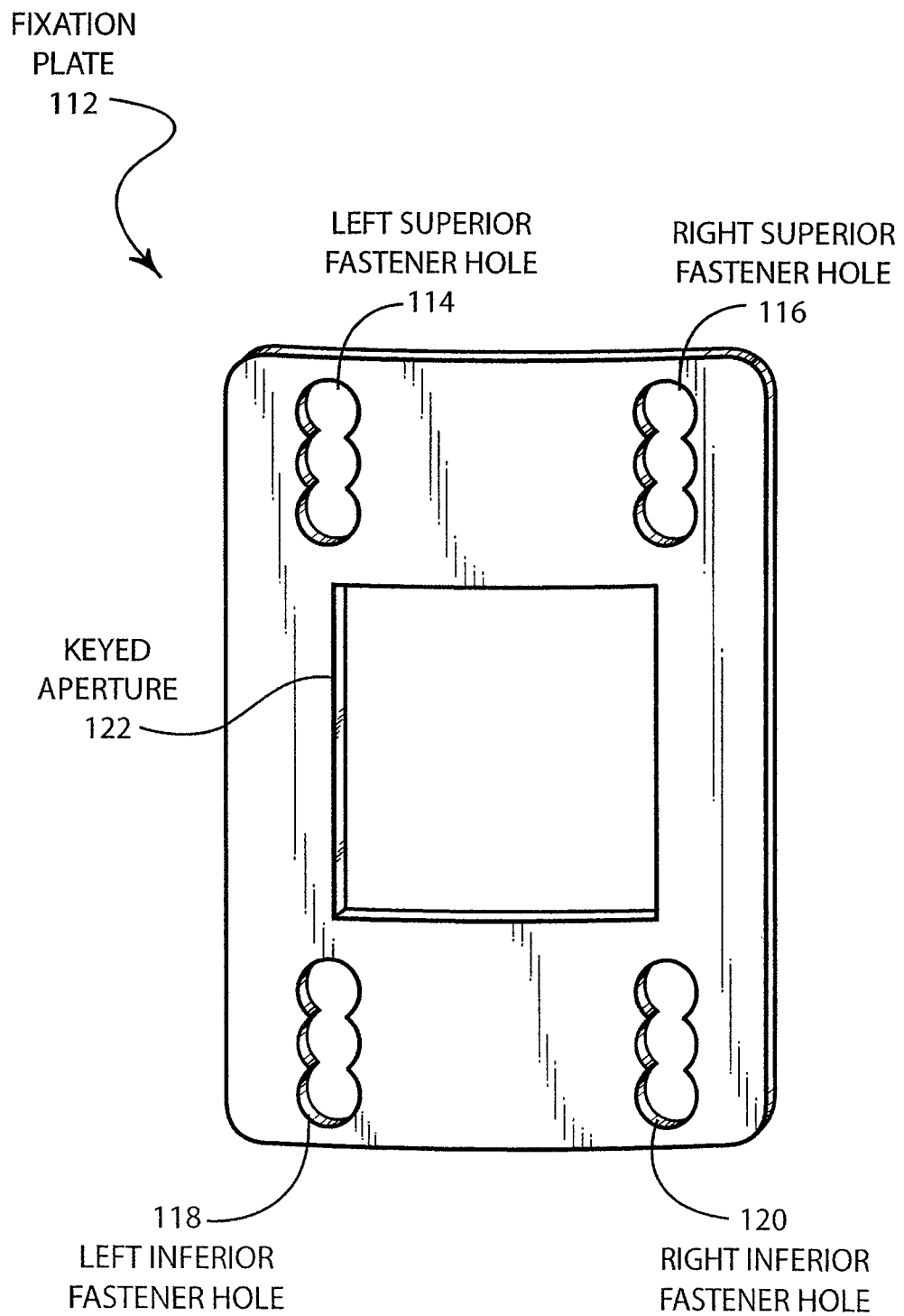
FIG. 3 is a perspective view of an embodiment of a fixation plate.

FIG. 3 is a perspective view of an embodiment of a fixation plate 112 such as that which can be utilized for lateral reduction and fusion of a section of a spine as detailed in FIG. 2. The fixation plate 112 is adapted for securing the stabilizer within the spine and is preferably made of a rigid biocompatible material such as titanium, stainless steel carbon fiber or the like. The plate may incorporate vertical curvatures as shown, which facilitate close contact with the vertebral body on either lateral or anterior sides but may also incorporate horizontal curvature (not shown) which may aid in maintaining anterior-posterior curvatures of the spine making the device applicable along the length of the spinal column including cervical, thoracic and lumbar regions.

As shown, the fixation plate 112 incorporates a series of fastener holes that can be readily adapted for locating fasteners in a variety of positions. These fastener holes are located substantially in the corners of the fixation plate 112 with each being depicted with multiple fixation points. With this particular embodiment, a fastener can be placed in any one of the fixation points within the fastener hole and allow minor rotation of the plate while maintaining its position with respect to the other fasteners. The variety of sizes, shapes and curvatures may be utilized for the fixation plate 112 in order to accommodate different size vertebrae and different applications and levels of vertebrae. For example, cervical, thoracic and lumbar regions may each have individually sized plates for both lateral and anterior placement.

As described above, the keyed aperture 122 allows visual and physical access to the intervertebral space and facilitates placement of the fixation plate 112 as well as providing access for insertion and manipulation of the stabilizer (graft or implant). A second function of the keyed aperture 122 is to provide a contact point for a positioning tool that can be temporarily mated with fixation plate 112 to impart force upon the plate and affixed vertebrae thereby positioning the vertebrae into proper alignment for fusion. The keyed aperture 122 is created of sufficient size to allow close visual inspection of the intervertebral space and the interface between a graft/implant. The aperture may additionally aid in the ultimate determination of the fastener location. Whereas a rectangular or square shaped keyed aperture 122 is depicted in FIG. 3, it falls within the scope of the described embodiments to allow various shaped apertures such as hexagonal, octagonal, trapezoidal, rounded rectangle, oval or the like which allow mating with a positioning tool and access through the aperture for a stabilizer.

Figure 4:
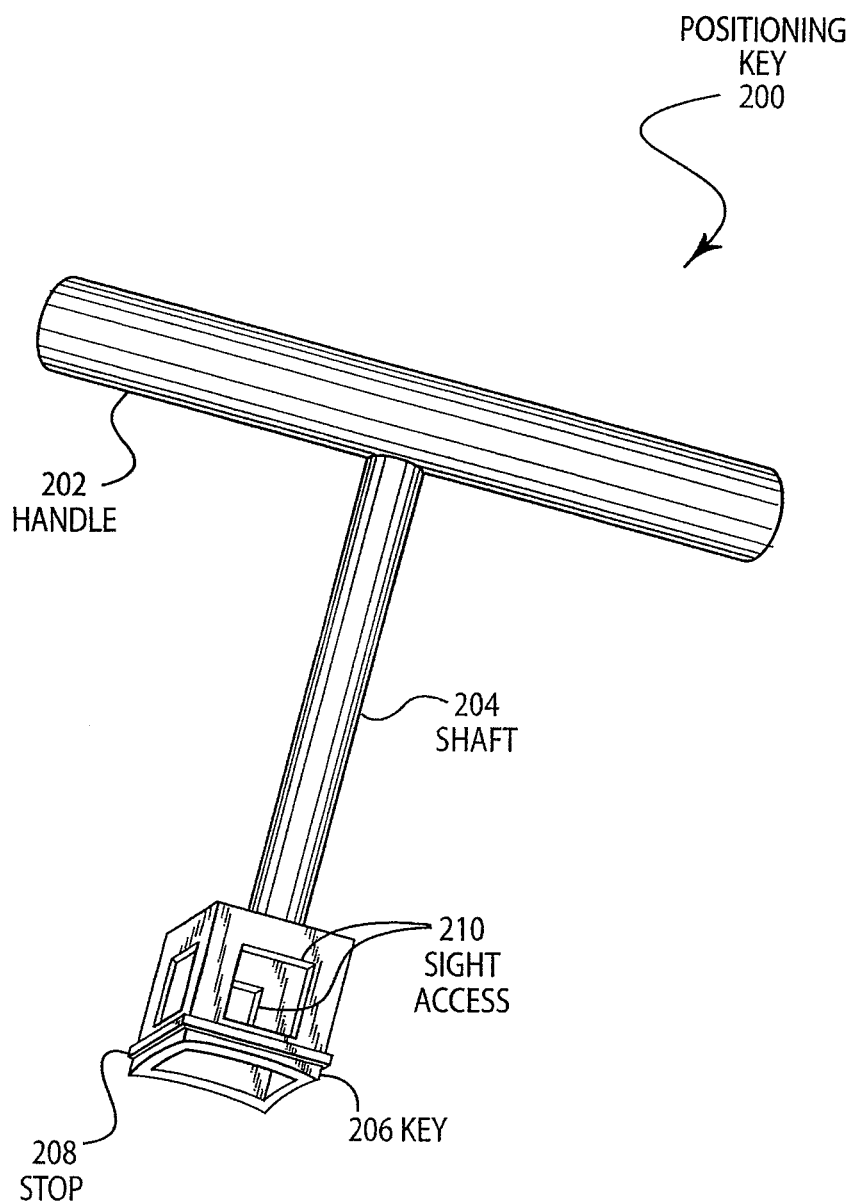
FIG. 4 is a perspective view of an embodiment of a positioning key for manipulation and positioning a fixation plate and affixed vertebrae.

FIG. 4 is a perspective view of an embodiment of a positioning key 200 for manipulation and positioning a fixation plate and affixed vertebrae. As previously mentioned, fixation plate 112 is loosely secured to two adjacent vertebrae that are in the process of being fused. A positioning key 200 comprises a grip or handle 202 that is connected to a key 206 by a rigid or semi-rigid shaft 204 that allows the transmission of translational or rotational force from the handle 202 to the key 206. The key 206 may additionally have sight access 210 in the form of ports or holes that allow the user greater visual access of the tool and its interface with the fixation plate 112.

The key 206 inserts into keyed aperture 122 of the fixation plate 112 to a depth of approximately the thickness of the plate. The external surface of the key 206 mates with the internal surface of the keyed aperture 122 and a stop 208 prevents the key from being inserted too far. Once inserted, the positioning key 200 can be rotated to impart rotational force on the fixation plate 112, and through the fasteners to the adjacent vertebrae. Similarly translational force can be imparted in the same manner giving the user mechanical advantage to easily and precisely guide the vertebrae into alignment and proper position for fusion.

Figure 5:
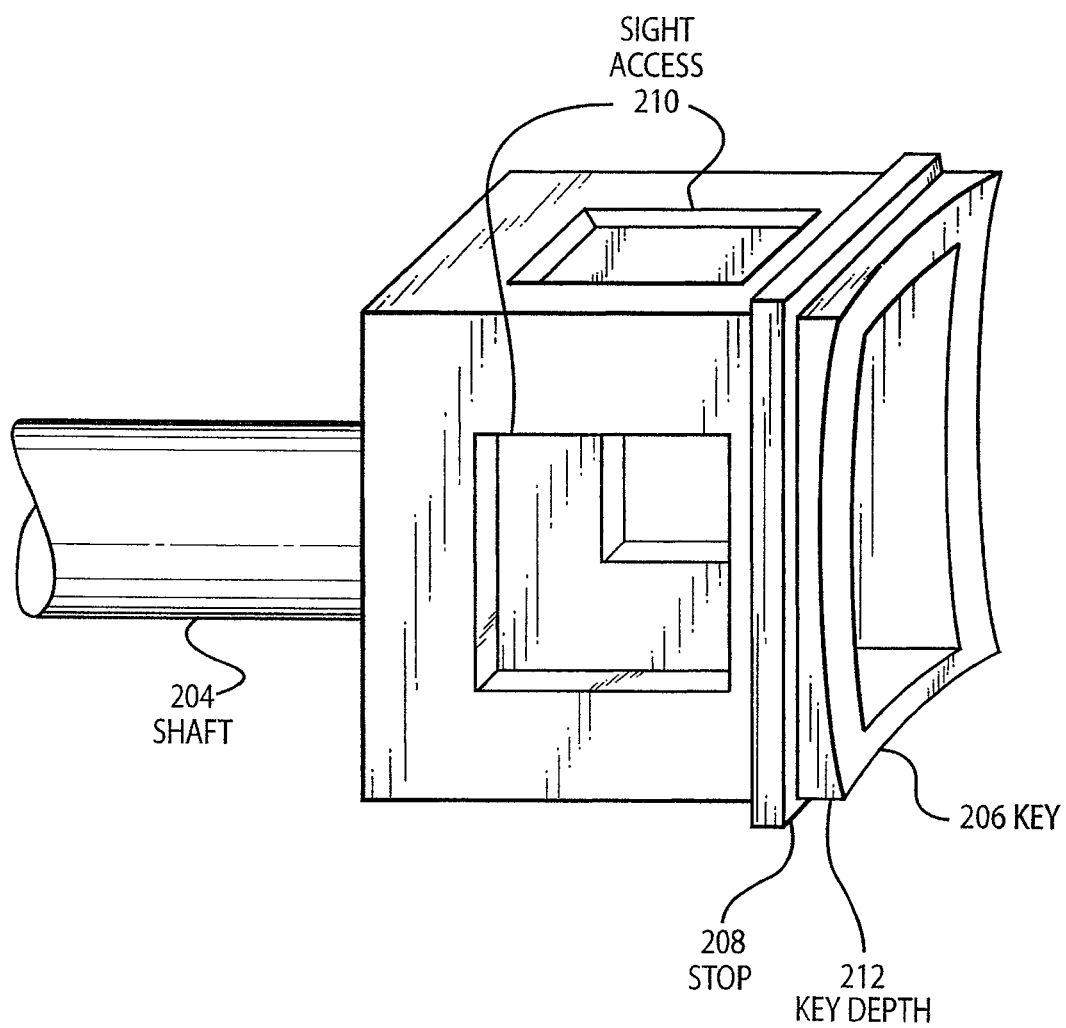
FIG. 5 is a detailed perspective view of an embodiment of a positioning key for manipulation and positioning a fixation plate and affixed vertebrae.

FIG. 5 is a detailed perspective view of an embodiment of a positioning key 200 for manipulation and positioning a fixation plate and affixed vertebrae. As shown in FIG. 5, the key 206 is approximately cubical but can be a variety of shapes which will allow it to impart force from the handle 202 and shaft 204 to the fixation plate 112. The key depth 212, or the distance that the key 206 can be inserted into the plate, is regulated by a stop 208 that contacts the plate surface giving the user positive tactile feedback that the key 206 is properly engaged.

Figure 6A:
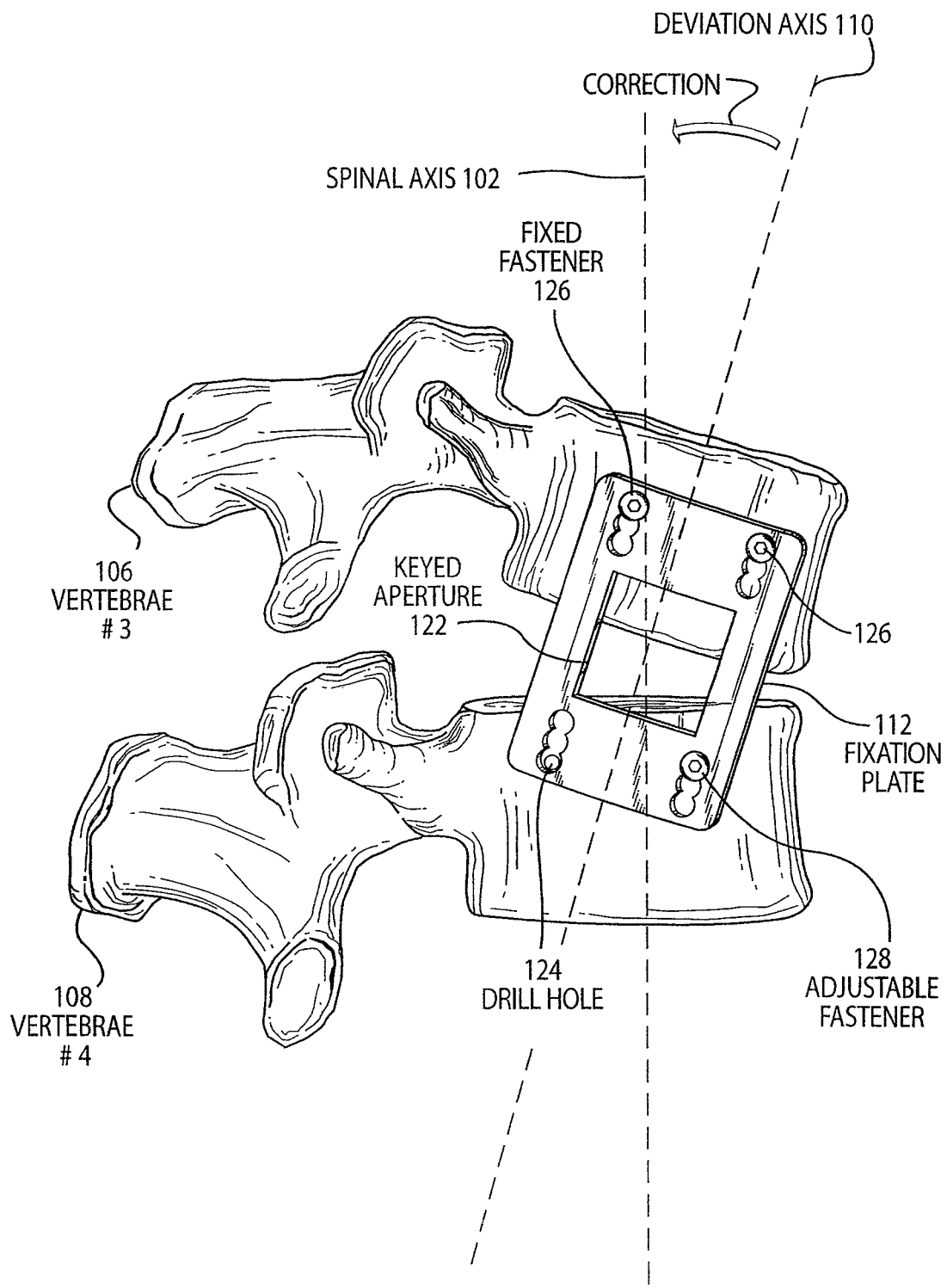
FIG. 6A is a lateral view of an embodiment of a fixation plate prior to being positioned using a positioning key to laterally reduce anterolisthesis of a section of a spine such as depicted in FIG. 2.
Figure 6B:
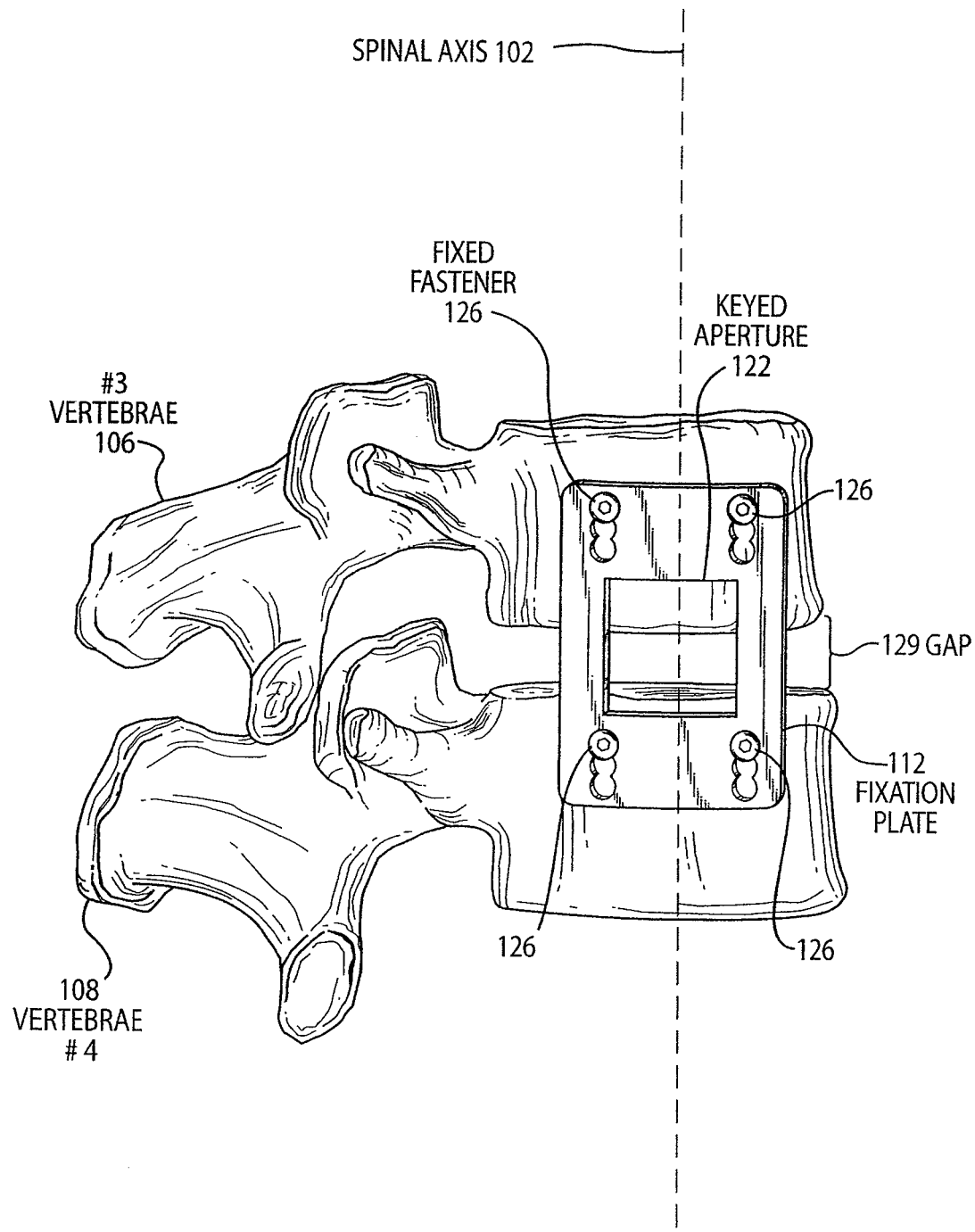
FIG. 6B is a lateral view of an embodiment of a fixation plate that has been positioned using a positioning key to laterally reduce anterolisthesis of a section of a spine such as depicted in FIG. 2.

FIGS. 6A and 6B are lateral views of an embodiment of a fixation plate 112 being positioned using a positioning key 200 to laterally reduce anterolisthesis of a section of a spine such as depicted in FIG. 2. Once the fixation plate 112 has been secured to vertebrae #3 106, in the manner described in FIG. 2 using fixed fasteners 126, the key 206 of the positioning key 200 is inserted into the key aperture 122 until the stop 208 contacts the surface of the plate. Pressure may now be exerted by the user to align vertebrae #3 106 and align vertebrae #4 108 for fusion using the adjustable fastener 128 as a pivot for the rotation. In the particular condition described in FIG. 2, a counter clockwise rotation of the handle will distract the disc space and reduce the vertebral body. A stabilizer may now be placed in the intervertebral space utilizing the keyed aperture 122. Once the stabilizer (graft) is in place, the tool is used to maintain the desired reduction. The clamp may then be inserted into the protruding fastener heads between the vertebrae to compress the graft. With the vertebrae now aligned and positioned, the left inferior fastener hole 118 is in proper position with respect to vertebrae #4 108, and drill hole 124 can be bored such that a fastener may be placed therein. At this point all fasteners may be tightly secured forming fixed fasteners 126 providing a rigid, stable, precise, translated fixation between the adjacent vertebrae that leaves access to the intervertebral space formed by a gap 129 containing the stabilizer.

Figure 7:
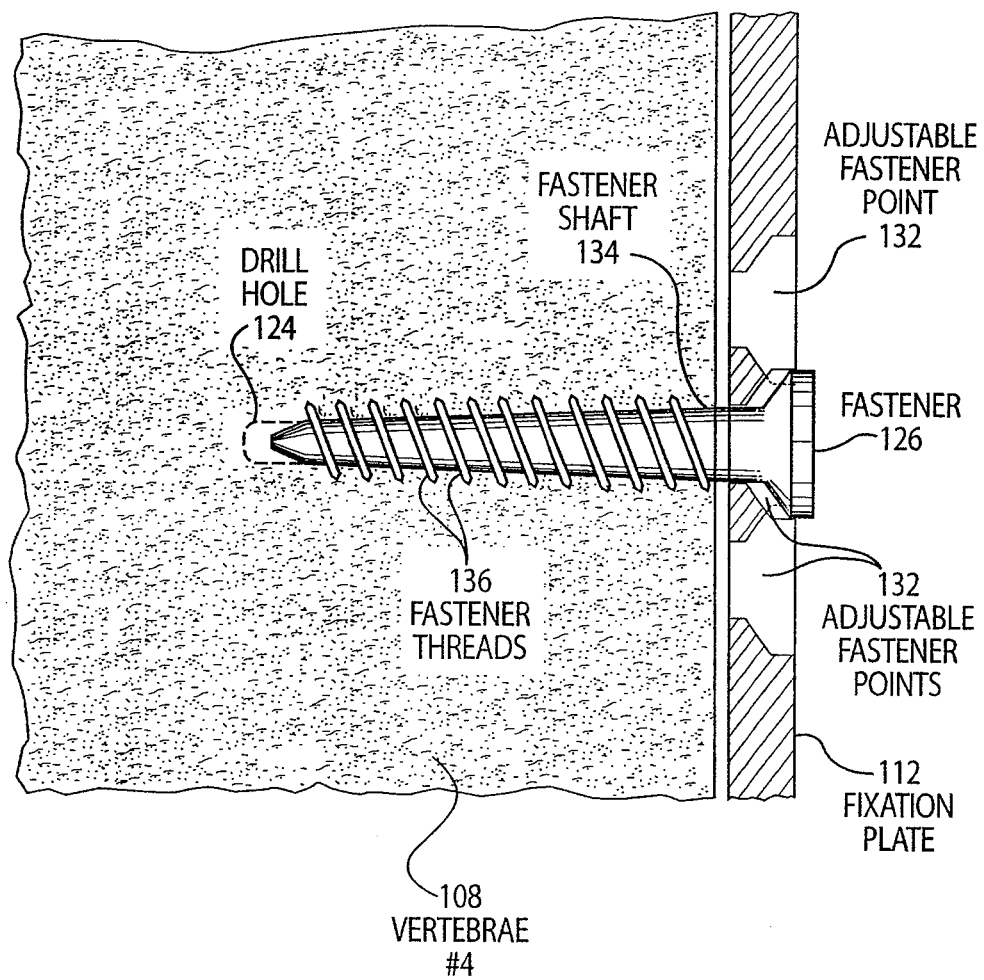
FIG. 7 is a lateral section view of an embodiment of a fixation plate that has been secured to a vertebral wall with threaded fasteners.

FIG. 7 is a lateral section view of an embodiment of a fixation plate 112 that has been secured to a vertebral wall with threaded fasteners. As shown in FIG. 7, a fixation plate 112 is placed in contact with the vertebral body of vertebrae #4 108, such as was shown in FIG. 2. A drill hole 124 is bored into the bone tissue and a threaded fastener 128 is placed through an adjustable fastener point 132 and screwed into position. The threaded fastener 128 shown in this example incorporates a fastener shaft 134 that provides a smooth cylindrical surface and allows rotation of the fixation plate about the adjustable fastener point 132 when the fastener 128 is not fully tightened. The adjustable fastener point 132 has multiple positions for which a fastener 128 may be positioned thereby allowing greater flexibility in setting the distance between adjacent vertebrae. The adjustable fastener points 132 may also be an elongated groove or slot that also allows the flexible positioning of the fixation plate 112 prior to fully tightening fasteners 128.

The fasteners 128 are ultimately inserted into the bone to a sufficient depth such that the fixation plate 112 cannot freely move with respect to the surface of the vertebrae, but may enable a small amount of movement under substantial force, thereby accommodating a small amount of natural shifting that occurs during the fusion between the stabilizer/graft and the adjacent vertebrae. The fasteners may also include a lock or locking mechanism such as a lock washer, lock plate, locking fastener head, ridged fastener holes, or the like to prevent any reverse rotation or withdrawal from the bone and fixation plate.

Traditionally, approaches to spine surgery have necessitated prolonged recovery time because a large incision was used to visualize the affected disc. In order to perform this procedure, large sections of the back muscles are moved away from their spinal attachments. This traditional surgical approach (i.e., dissecting the muscles) produces the majority of the perioperative pain and delays return to full activity and may necessitate the use of significant pain medication and delays return to normal activity. Additionally, the dissection of the paraspinal muscles from their normal anatomic points of attachment results in scarring of these muscles. The various layers of the individual muscle scar to one another thereby decrease their independent function. Furthermore, it has been found that this type of dissection sometimes results in the loss of innervation (i.e., the supply of nerve stimulation) of the muscles with subsequent wasting away resulting in a permanent weakness of the back muscles. By utilizing the aforementioned methods and devices, the surgeon may perform lateral reduction and fusion procedure in a minimally invasive manner.

In conventional fusion surgery, the surgeon starts by correcting the spinal alignment with a contemporary correction instrument that typically includes rods that are intended to be attached to the vertebrae. Once in place, these rods obstruct the fitting of plates used to stabilize the spine. If the correction instrument is removed prior to definitive fixation of the plate, it is necessary to make adjustments in the plate alignment prior to ultimate fixation.

By attaching the fixation plate 112 to the vertebrae, and then adjusting the vertebral orientation with the positioning key 200, no correction instrument rods are used and there is therefore, no interference between the rods and the plate. This allows the surgeon to use less instrumentation, tools and hardware in the surgical procedure thereby reducing incision size and enabling access to the spine in a more lateral manner thereby avoiding the large muscle masses immediately lateral and dorsal to the spine.

Figure 8:
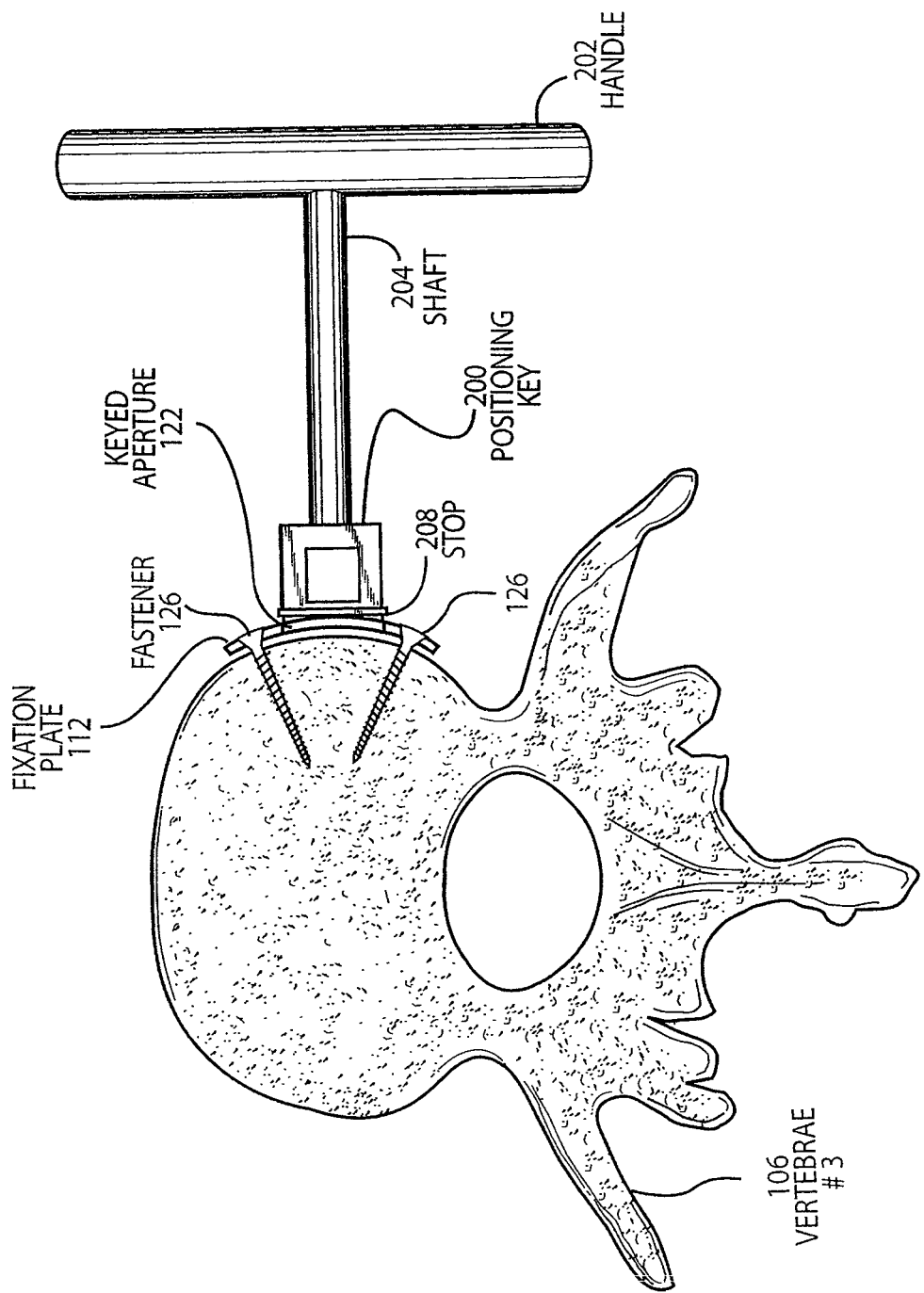
FIG. 8 is a superior transverse section view of an embodiment of a fixation plate that has been positioned using a positioning key and secured to a lateral vertebral wall utilizing threaded fasteners such as depicted in FIG. 6.

FIG. 8 is a superior transverse section view of an embodiment of a fixation plate 112 that has been positioned using a positioning key 200 and secured to a lateral vertebral wall utilizing threaded fasteners such as depicted in FIG. 6. As shown in FIG. 8, fixation plate 112 is curved to match the surface of the lateral vertebral wall facilitating good contact between the plate and bone. Threaded fixed fasteners 126 secure the fixation plate 112 and may be placed in a radial orientation with respect to the spinal axis 102 of vertebra #3 106. The keyed aperture 122 maintains a transverse cut through the fixation plate 112 in order to facilitate contact with the key 206 of the positioning key 200. It is clear from FIG. 8 that a force created by twisting of the handle of the positioning key 200 can be translated through the fixation plate 112 to the vertebra #3 106.

Figure 9:
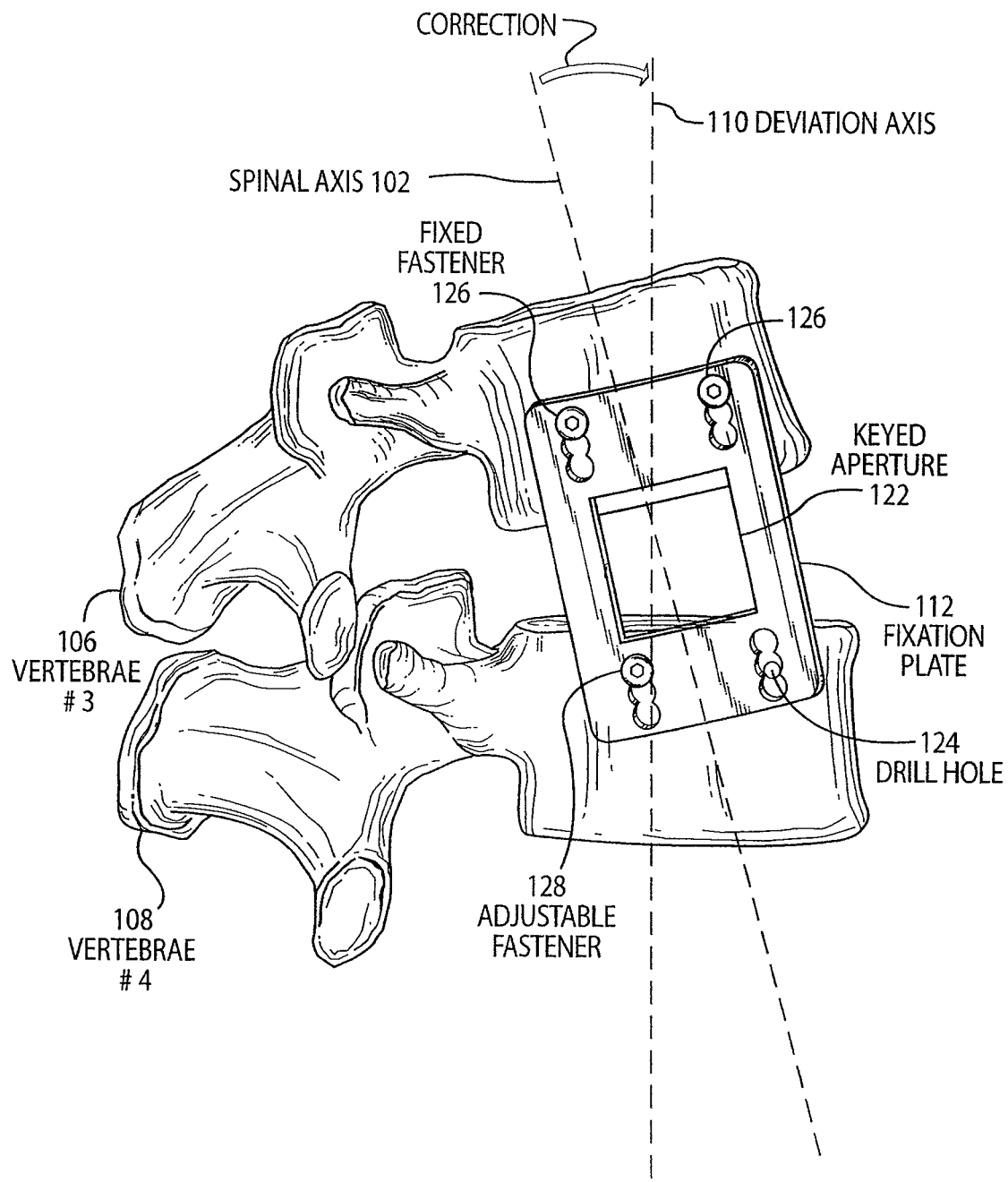
FIG. 9 is a lateral view of an embodiment of a fixation plate utilized for a lateral reduction and fusion of a section of a spine that is experiencing retrolisthesis.

FIG. 9 is a lateral view of an embodiment of a fixation plate 112 utilized for a lateral reduction and fusion of a section the spine that is experiencing retrolisthesis. In a manner similar to that depicted in FIG. 2 a fixation plate 112 is positioned on the lateral aspect of the vertebral body of abnormally displaced vertebrae #3 106, anterior of the pedicle. Assuming also in this case that the disc between vertebrae #3 106 and vertebrae #4 108 has already been removed by conventional means, proper alignment and spacing and of these two adjacent discs is now performed. As illustrated, fixation plate 112 is positioned in general alignment with the deviation axis 110 of vertebrae #3 106. One or two drill holes 124 are bored into the vertebral body of vertebrae #3 106 corresponding to the position of left superior fastener hole 114 and/or right superior fastener hole 116.

Fasteners, such as those depicted in FIG. 7 are then placed into the drill hole(s) and secured leaving a small gap between the head of the fastener and the fixation plate 112 to allow for rotational movement of the device. Once vertebrae #3 106 has been slideably attached to the fixation plate 112, the proper distance between the adjacent vertebrae can be set by positioning an additional drill hole 124 on vertebrae #4 108 corresponding with the left inferior fastener hole 118 of fixation plate 112. An additional fastener may then be placed into the drill hole 124 through the left inferior fastener hole 120 and secured similar to the fasteners secured into vertebrae #3 106 allowing rotational movement of the device. No fastener is placed in the right inferior fastener hole 120 at this time because the fixation plate 112 is not ultimately positioned with respect to vertebrae #4 108. As was performed in the example of FIG. 2, the distance between the adjacent vertebrae is set by the relative position of the fixation plate 112 and the fasteners secured to the vertebrae.

Figure 10:
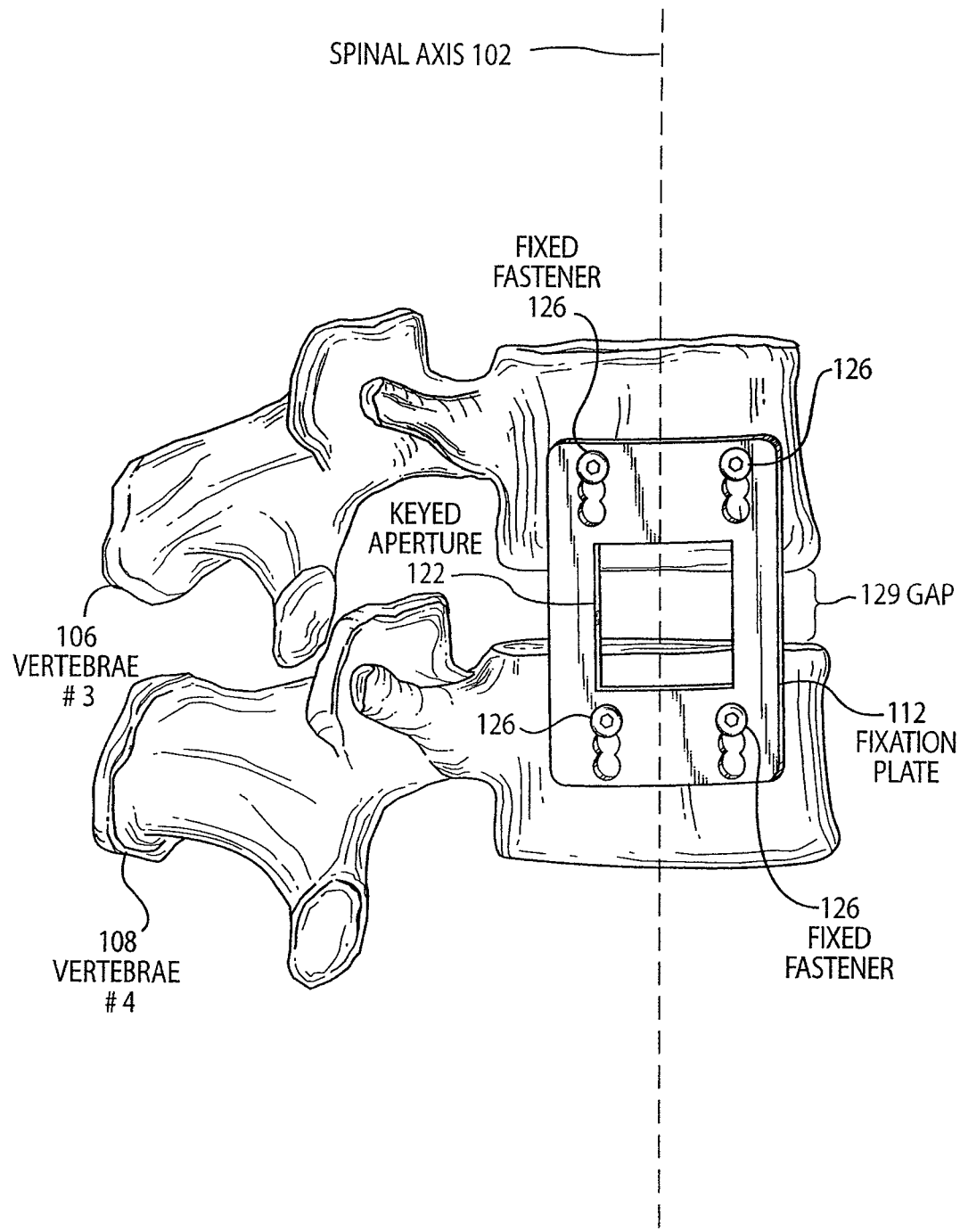
FIG. 10 is a lateral view of an embodiment of a fixation plate that has been positioned using a positioning key to laterally reduce retrolisthesis of a section of a spine such as depicted in FIG. 9.

FIG. 10 is a lateral view of an embodiment of a fixation plate 112 that has been positioned using a positioning key 200 to laterally reduce retrolisthesis of a section of a spine such as depicted in FIG. 9. Once the fixation plate 112 has been secured to vertebrae #3 106, the key 206 of the positioning key 200 is inserted into the key aperture 122 until the stop 208 contacts the surface of the plate. Pressure may now be exerted by the user to align vertebrae #3 106 and align vertebrae #4 108 for fusion. In the particular condition described in FIG. 9, a clockwise rotation of the handle will distract the disc space and reduce the vertebral body. A stabilizer may now be placed in the intervertebral space utilizing the keyed aperture 122. Once the graft is in place, the tool is used to maintain the desired reduction. The clamp may then be inserted into the protruding fastener heads between the vertebrae to compress the graft. With the vertebrae now aligned and positioned, the right inferior fastener hole 120 is in proper position with respect to vertebrae #4 108 and drill hole 124 can be bored such that a fastener may be placed therein. At this point all fasteners may be tightly secured forming fixed fasteners 126 providing a rigid, stable, precise, translated fixation between the adjacent vertebrae that leaves access to the intervertebral space formed by a gap 129 containing the graft.

Figure 11:
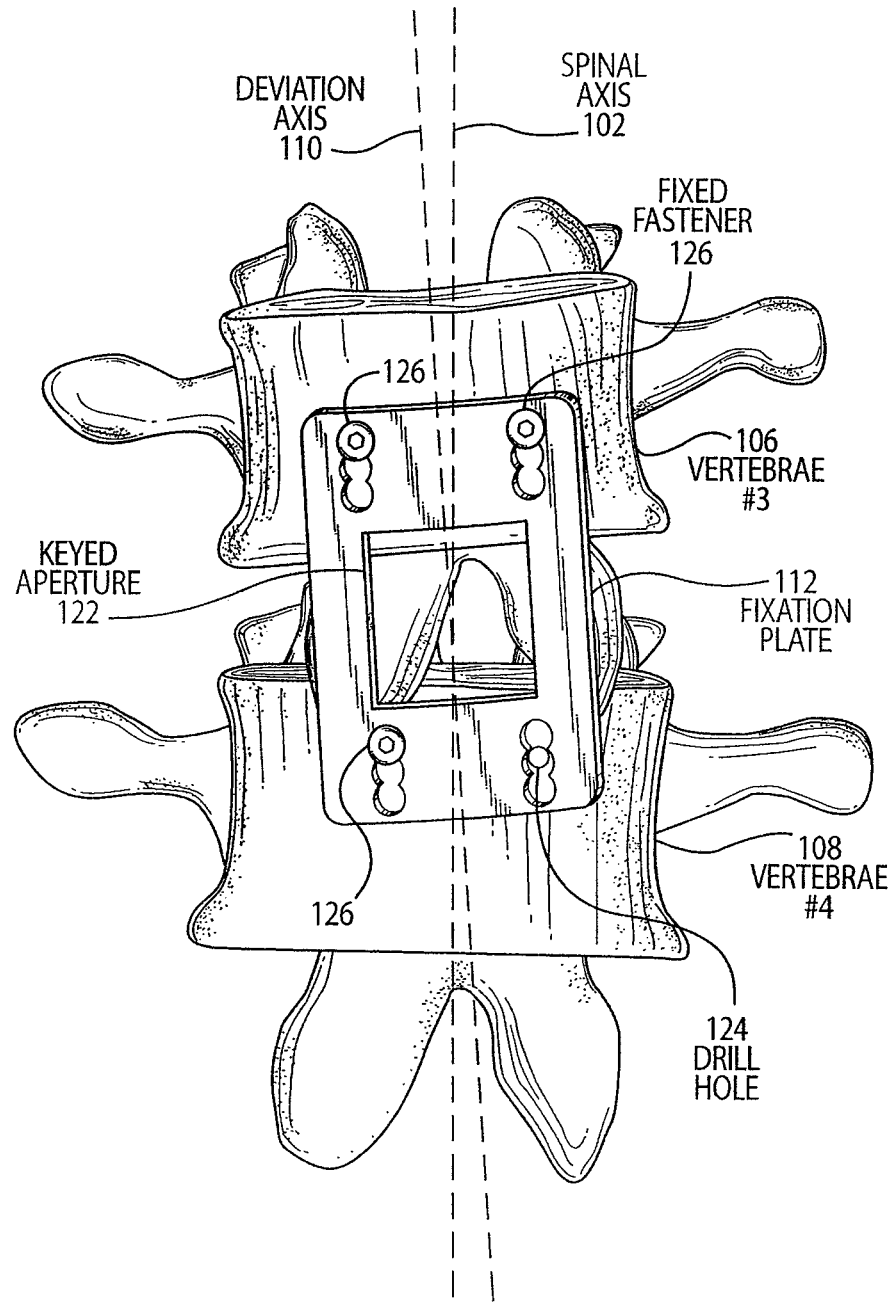
FIG. 11 is an anterior view of an embodiment of a fixation plate utilized for angular reduction and fusion of a section of a spine that is experiencing lateral slip.

FIG. 11 is an anterior view of an embodiment of a fixation plate 112 utilized for angular reduction and fusion of a section the spine that is experiencing lateral slip. In a manner similar to that depicted in FIG. 2 a fixation plate 112 is positioned on the anterior aspect of the vertebral body of abnormally displaced vertebrae #3 106. Assuming also in this case, that the disc between vertebrae #3 106 and vertebrae #4 108 has already been removed by conventional means, proper alignment and spacing of these two adjacent discs is now performed. In a manner similar to that detailed in FIGS. 2 and 9, fixation plate 112 is positioned in general alignment with the deviation axis 110 of vertebrae #3 106. One or two drill holes 124 are bored into the vertebral body of vertebrae #3 106 corresponding to the position of left superior fastener hole 114 and/or right superior faster hole 116. Fasteners, such as those depicted in FIG. 7 are then placed into the drill hole(s) and secured leaving a small gap between the head of the fastener and the fixation plate 112 to allow for rotational movement of the device. Once vertebrae #3 106 has been slideably attached to the fixation plate 112, the proper distance between the adjacent vertebrae can be set by positioning an additional drill hole 124 on vertebrae #4 108 corresponding with the left inferior fastener hole 118 of fixation plate 112. An additional fastener may then be placed into the drill hole 124 through the left inferior fastener hole 120 and secured similar to the fasteners secured into vertebrae #3 106 allowing rotational movement of the device. No fastener is placed in the right inferior fastener hole 120 at this time because the fixation plate 112 is not ultimately positioned with respect to vertebrae #4 108. As was performed in the example of FIGS. 2 and 9, the distance between the adjacent vertebrae is set by the relative position of the fixation plate 112 and the fasteners secured to the vertebrae.

Figure 12:
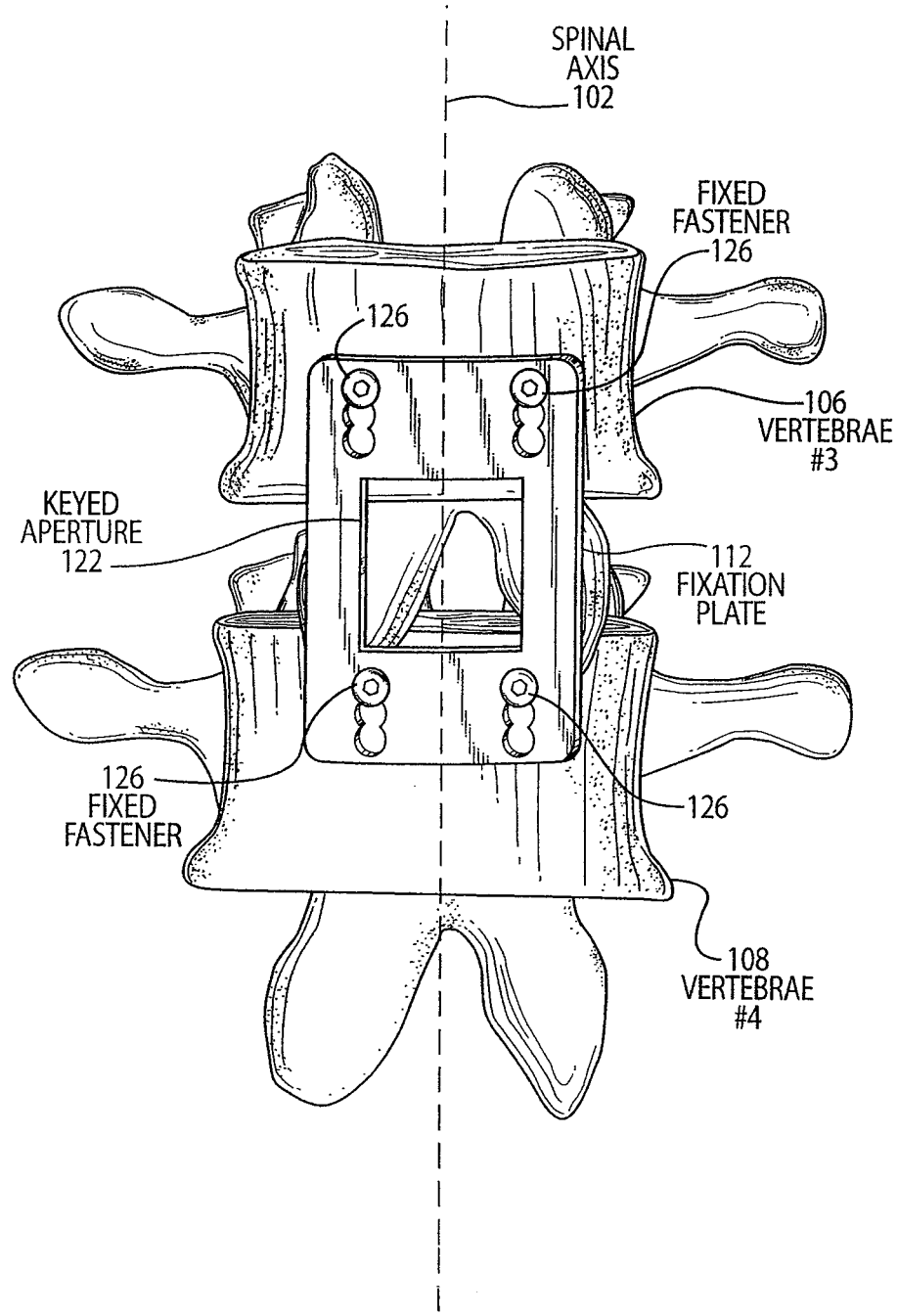
FIG. 12 is an anterior view of an embodiment of a fixation plate that has been positioned using a positioning key to reduce lateral slip of a section of a spine such as depicted in FIG. 11.

FIG. 12 is an anterior view of an embodiment of a fixation plate that has been positioned using a positioning key to reduce lateral slip of a section of a spine such as depicted in FIG. 11. Once the fixation plate 112 has been secured to vertebrae #3 106, the key 206 portion of the positioning key 200 is inserted into the key aperture 122 until the stop 208 contacts the surface of the plate. Pressure may now be exerted by the user to align vertebrae #3 106 and align vertebrae #4 108 for fusion. In the particular condition described in FIG. 12, a clockwise rotation of the handle will distract the disc space and reduce the vertebral body. A graft or implant may now be placed in the intervertebral space utilizing the keyed aperture 122. Once the graft is in place, the tool is used to maintain the desired reduction. The clamp may then be inserted into the protruding fastener heads between the vertebrae to compress the graft. With the vertebrae now aligned and positioned, the right inferior fastener hole 120 is in proper position with respect to vertebrae #4 108 and drill hole 124 can be bored such that a fastener may be placed therein. At this point all fasteners may be tightly secured forming fixed fasteners 126 providing a rigid, stable, precise, translated fixation between the adjacent vertebrae that leaves access to the intervertebral space containing the graft.

Figure 13:
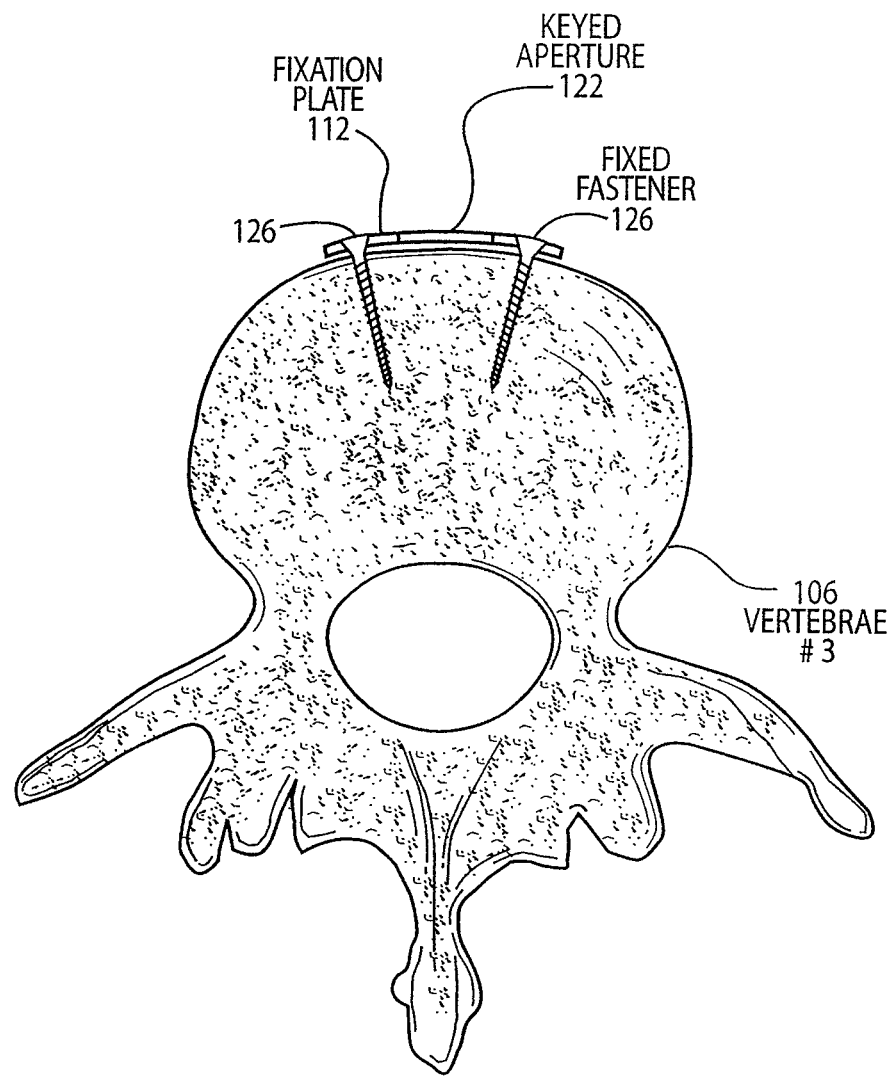
FIG. 13 is a superior transverse section view of an embodiment of a fixation plate that has been secured to an anterior vertebral wall utilizing threaded fasteners such as depicted in FIG. 12.

FIG. 13 is a superior transverse section view of an embodiment of a fixation plate 112 that has been secured to an anterior vertebral wall utilizing threaded fasteners such as depicted in FIG. 12. As shown in FIG. 13, fixation plate 112 is curved to match the surface of the anterior vertebral wall facilitating good contact between the plate and bone. Threaded fixed fasteners 126 secure the fixation plate 112 and may be placed in a radial orientation with respect to the spinal axis 102 of vertebra #3 106. The keyed aperture 122 maintains a transverse cut through the fixation plate 112 in order to facilitate contact with the key 206 of the positioning key 200.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

The invention claimed is:

1. A system for manipulating vertebral orientation of and stabilizing adjacent spinal vertebrae comprising:
   a fixation plate having a central Keyed aperture and a plurality of first-end fastener holes and a plurality of second-end fastener holes positioned on opposing ends of said fixation plate;
   at least one fixed fastener that secures a first vertebrae through said first-end fastener holes and fixate position and rotation of said first-end of said fixation plate with respect to said first vertebrae;
   an adjustable fastener that secures a second vertebrae through said second-end fastener holes to temporarily fixate position and allows rotation of said second-end of said fixation plate with respect to said second vertebrae;
   a positioning tool that is keyed to interface with said Keyed aperture of said fixation plate and engages said aperture to adjust the orientation of said first vertebrae relative to said second vertebrae by transferring force from said positioning tool through said fixation plate to said first vertebrae and said second vertebrae;
   a stabilizer for implantation between said first vertebrae and said second vertebrae through said Keyed aperture;
   said second-end fastener holes that facilitate repositioning of said adjustable fastener to vary the distance between said fixed fastener and said adjustable fastener to compress said stabilizer between said first vertebrae and said second vertebrae and rigidly secure position and rotation of said adjustable fastener to said second vertebrae.

2. The system of claim 1 further comprising:
   said fixation plate that has a substantially rectangular shape.

3. The system of claim 1 further comprising:
   said fixation plate that has an arc shape to approximately match a vertebral body curve of said first and second vertebrae.

4. The system of claim 1 further comprising:
   said central Keyed aperture that has a center point that is substantially coincident with the spinal axis at a point approximately equidistant from said first and second vertebrae.

5. The system of claim 1 wherein said central Keyed aperture further comprises an opening of sufficient size to accommodate insertion of said stabilizer.

6. The system of claim 1 wherein said plurality of first-end fastener holes further comprises:
   a pair of circular holes.

7. The system of claim 1 wherein said plurality of first-end fastener holes further comprises:
   a pair of longitudinally extending slots.

8. The system of claim 1 wherein said plurality of second-end fastener holes are spaced substantially equidistant from the center of said fixation plate.

9. The system of claim 1 wherein said plurality of second-end fastener holes further comprises a pair of longitudinally extending slots.

10. The system of claim 1 wherein said second-end fastener holes accommodate multiple fixation points for said adjustable fasteners comprise said fixed fasteners.

11. The system of claim 1 wherein said fixed fasteners are threaded fasteners.

12. The system of claim 1 wherein said adjustable fasteners are threaded fasteners that have not been tightened into said second vertebrae.

13. The system of claim 1 further comprising:
    a lock that prevents withdrawal of said fixed fasteners from said fixation plate.

14. The system of claim 1 wherein said positioning tool further comprises:
    a shaft connecting a key for engaging and transferring force from a handled grip to said Keyed aperture.

15. The system of claim 1 wherein said positioning tool further comprises:
    a sight access that allows visual inspection of said aperture through said positioning tool.

16. The system of claim 1 wherein said stabilizer is selected from the group consisting of a bone graft, a spinal implant, and an artificial disc.

17. A system for manipulating vertebral orientation of and stabilizing adjacent spinal vertebrae comprising:
    means for fixing position and rotation of a first-end of a fixation plate to a first vertebrae with a fixed fastener;
    means for temporarily fixing position and allowing rotation of a second-end of said fixation plate to a second vertebrae with an adjustable fastener;
    means for adjusting orientation of said first vertebrae with respect to said second vertebrae by engaging a central Keyed aperture on said fixation plate with a positioning tool that is keyed to interface with said central Keyed aperture;
    means for compressing a stabilizer that is inserted between said first vertebrae and said second vertebrae through said central Keyed aperture by adjusting a distance between said second-end of said fixation plate; and,
    means for fixing said distance between said first vertebrae and said second vertebrae by securing position and rotation of said second-end of said fixation plate to said second vertebrae.

* * * * *